United States Patent
Bak et al.

(10) Patent No.: US 6,350,936 B1
(45) Date of Patent: Feb. 26, 2002

(54) GUZMANIA PLANT NAMED 'COPITO'

(75) Inventors: Elly Bak, Rijsenhout; Nicolaas D. M. Steur, Oude Niedorp, both of (NL)

(73) Assignee: CORN. BAK B.V., Assendelft (NL)

( * ) Notice: Subject to any disclaimer, the term of this patent is extended or adjusted under 35 U.S.C. 154(b) by 0 days.

(21) Appl. No.: 09/630,135

(22) Filed: Aug. 1, 2000

Related U.S. Application Data

(63) Continuation-in-part of application No. 09/572,314, filed on May 18, 2000.

(51) Int. Cl.⁷ .............................. A01H 5/00; A01H 1/00; A01H 1/02
(52) U.S. Cl. ..................... 800/298; 800/260; 800/323
(58) Field of Search ................................. 800/298, 260, 800/323; Plt./371

(56) References Cited

U.S. PATENT DOCUMENTS

PP8,996 P * 11/1994 Bak et al. ................... Plt./371

* cited by examiner

Primary Examiner—Bruce R. Campell
Assistant Examiner—Kent L. Bell
(74) Attorney, Agent, or Firm—Foley & Lardner

(57) ABSTRACT

A Guzmania plant named 'Copito' particularly characterized by its solid growth habit in a funnel-form rosette measuring approximately 20 cm in height above the pot when flowering; numerous, relatively narrow leaves, each approximately 2–2.5 cm in width and 25 cm in length; superior floral bract production; compound inflorescence; and long-lasting habit.

5 Claims, 2 Drawing Sheets

(2 of 2 Drawing Sheet(s) Filed in Color)

GUZMANIA PLANT NAMED 'COPITO'

This is a continuation-in-part application of U.S. patent application Ser. No. 09/572,314, filed May 18, 2000, now pending.

FIELD OF INVENTION

The present invention relates to a new and distinct cultivar of Guzmania that is a hybrid, hereinafter referred to by the cultivar name 'Copito'. The present invention relates to seeds which are Guzmania cultivar 'Copito', as well as plants and plant parts produced from these seeds which have all the morphological and physiological characteristics of the Guzmania cultivar 'Copito'. The present invention also relates to methods for producing these seeds and plants. Furthermore, the present invention relates to a method of producing progeny Guzmania plants by crossing Guzmania cultivar 'Copito', as the male or female parent, with another Guzmania plant and selecting progeny.

BACKGROUND OF THE INVENTION

Guzmania is predominantly epiphytic with a few terrestrial species and is native to the tropics. For the most part, species vary in diameter from 7 or 8 inches to 3 or 4 feet and have rosettes of glossy, smooth-edged leaves.

Floral bracts of Guzmania frequently have brilliant colors and may last for many months. The range of colors for Guzmania is generally from yellow through orange but may also include flame red and red-purple. White or yellow, tubular, three-petalled flowers may also appear on a stem or within the leaf rosette but are usually short-lived.

Guzmania may be advantageously grown as pot plants for greenhouse or home use. Typically, the plants are shaded from direct sunlight. During the spring to autumn period, the central vase-like part of the leaf rosette is normally filled with water.

Guzmania is native to tropical America. Leaves of Guzmania are usually formed as basal rosettes which are stiff and entire and in several vertical ranks. Guzmania plants have terminal spikes or panicles which are often bracted with petals united in a tube about as long as the calyx. The ovary is superior and the seeds plumose.

Asexual propagation of Guzmania is frequently done through the use of tissue culture practices. Propagation can also be from offshoots which can be detached from the mother plant and grown in an appropriate soil or bark mixture.

Methods for cultivation and crossing of Guzmania are well known. For a detailed discussion, reference is made to the following publications, which are incorporated herein by reference: Benzing, David H., *THE BIOLOGY OF THE BROMELIADS*, Mad River Press, Inc., Eureka (1980); Zimmer, Karl, *BROMELIEN*, Verlag Paul Parey, Berlin (1986); and Rauh, Werner, *BROMELIEN*, Verlag Eugen Ulmer, Stuttgart (1981).

A Guzmnania inbred is produced by brother/sister crossing over several generations to produce a genetically homozygous plant selection. A hybrid cultivar is produced by crossing two genetically distinct inbred lines, collecting seeds produced by the cross, and germinating seeds so-produced to make hybrid plants. The hybrid seeds and plants produced by this method are uniform with respect to their morphological and physiological characteristics.

A need exists for a greater variety of Guzrnania cultivars with attractive ornamental features. Additionally, a need exists for additional Guzmania hybrid cultivars that can be easily propagated by seed.

SUMMARY OF THE INVENTION

These and other objectives have been achieved in accordance with the present invention which provides a new cultivar 'Copito' that is a product of a planned breeding program undertaken by the inventors in Assendelft, The Netherlands, in 1994. The male or pollen parent was a selection of Guzmania lingulata minor identified by Code No. 94861137. The female or seed parent was a selection of Guzmania lingulata minor identified by Code No. 94861032.

Both parents have a sufficient degree of homozygosity such that the progeny of the cross are genetically and phenotypically uniform. The cultivar 'Copito' therefore can be produced by sexual reproduction by crossing 94861137× 94861032 to produce a population of progeny plants, each of which has the combination of characteristics as herein disclosed for the new cultivar. Seeds, which are cultivar 'Copito', are produced by crossing 94861137×94861032 and have been deposited with the American Type Culture Collection, 10801 University Boulevard, Manassas, Va. 20110-2209, and accorded Deposit Accession No. PTA-3263. 2500 seeds were deposited with the ATCC on Apr. 9, 2001.

The cultivar 'Copito' can also be produced by asexually reproducing progeny from the cross of 94861137×94861032 because the combination of characteristics as herein disclosed for the new cultivar 'Copito' are firmly fixed and are retained through successive generations of asexual reproduction.

OBJECTS OF THE INVENTION

This invention relates to seeds which produce Guzmania cultivar 'Copito'.

This invention also relates to Guzmnania plants, and parts thereof, having all the physiological and morphological characteristics of Guzmania cultivar 'Copito'. This invention relates to a plant produced from seeds which are Guzmania cultivar 'Copito'. This invention also relates to plant parts, such as pollen, seeds or inflorescence produced by Guzmania cultivar 'Copito'.

This invention relates to a method of producing seeds which are Guzmania cultivar 'Copito', by crossing Guzmania lingulata minor selection 94861032 as the female parent with Guzmania lingulata minor selection 94861137 as the male parent and the reciprocate cross with 94861032 as the male parent and 94861137 as the female parent and harvesting seeds produced from said crosses.

This invention also relates to a method of producing plants having all the physiological and morphological characteristics of the Guzmania cultivar 'Copito' comprising the steps of (a) crossing Guzmania lingulata minor selection 94861032 as the female parent with Guzmania lingulata minor selection 94861137 as the male parent; (b) harvesting seeds produced from said cross; and (c) producing plants from said harvested seeds.

The invention also relates to producing progeny plants from the cross of Guzmania cultivar 'Copito', as the male or female parent, with another Guzmania plant, and selecting progeny plants for this cross.

BRIEF DESCRIPTION OF THE FIGURES

The file of this patent contains at least one drawing executed in color. Copies of this patent with the color drawing(s) will be provided by the Patent and Trademark Office upon request and payment of the necessary fee.

DETAILED DESCRIPTION

Figure 1:
FIG. 1 is a side view of the inflorescence and foliage characteristics of 'Copito', with colors being as true as possible with illustrations of this type.
Figure 2:
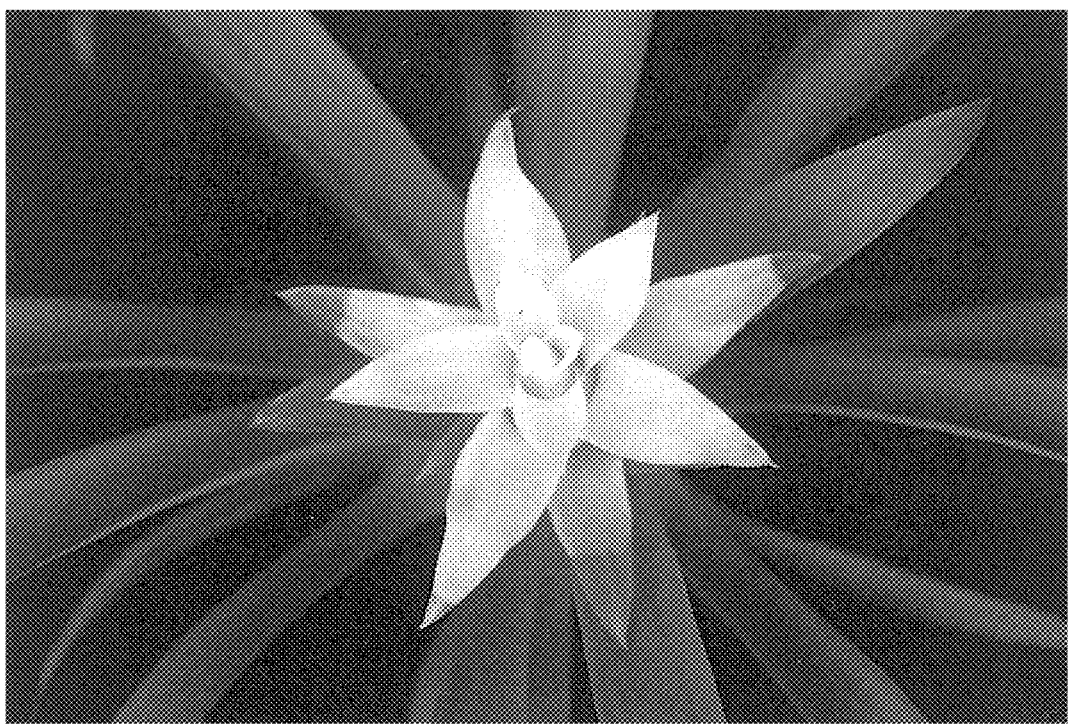
FIG. 2 is a close-up view of the inflorescence of 'Copito'.

This invention is directed to a Guzmania plant having all the morphological and physiological characteristics of the cultivar 'Copito' produced from seeds which are the product of the cross of Guzmania lingulata minor selection 94861032 as the female parent with Guzmania lingulata minor selection 94861137 as the male parent. Both parents have a sufficient degree of homozygosity such that the progeny of the cross were, and continue to be, phenotypically uniform. The variety 'Copito' therefore can be produced by sexual reproduction by crossing 94861032× 94861137 to produce a population of progeny plants each of which has the combination of characteristics as herein disclosed for the new cultivar.

The variety 'Copito' can also be produced by asexually reproducing progeny from the cross of 94861032×94861137 because the combination of characteristics as herein disclosed for the new cultivar 'Copito' are firmly fixed and are retained through successive generations of asexual reproduction. The selection comprising the new variety was chosen after commencement of flowering of the progeny in 1997 in Assendelft, The Netherlands. The selection was first asexually propagated through offshoots by, or under the supervision of, the inventors in Assendelft, The Netherlands, with subsequent asexual reproduction being primarily by offshoots. Sexual and asexual propagation has demonstrated that the combination of characteristics as herein disclosed for the new cultivar 'Copito', as observed in Assendelft, The Netherlands, are firmly fixed and are retained through successive generations of asexual reproduction.

'Copito' is particularly characterized by the following characteristics:

1. solid growth habit in a funnel-form rosette measuring approximately 20 cm in height above the pot when flowering;
2. numerous, relatively narrow leaves, each approximately 2–2.5 cm in width and 25 cm in length;
3. superior floral bract production;
4. compound inflorescence; and
5. long-lasting habit.

'Copito' has not been tested under all available environmental conditions. The phenotype may vary with variations in environmental conditions such as temperature, light intensity, frequency of fertilization, composition of fertilizer, acetylene treatment, day length and humidity without, however, any change in the genotype of the new cultivar.

For example, substantial differences in plant height and diameter, and the number of leaves, can result depending on the size of the plant at the time flowering is induced by acetylene treatment. Since treatment with acetylene to induce flowering disrupts normal watering and fertilization regimens, acetylene treatment of relatively smaller plants adversely affects the growth of the plant.

The following traits have been repeatedly observed and in combination distinguish 'Copito' as a new and distinct cultivar. These observations, measurements and descriptions were taken for 'Copito' plants grown under the following greenhouse conditions in Assendelft, The Netherlands. The minimum day and night temperatures were 20° C. and 18° C., respectively. The ventilation temperature was 24° C., and the maximum light intensity was 18000 Lux. Fertilizer concentration was 0.5 to 1 EC comprising N:P:K in the ratio of 1:0.25 to 0.5:2 to 3. In addition, 3% of the total amount of fertilizer was $MgSO_4$(15% MgO).

Frequency of fertilization varied depending on time of year and ranged from once per week to once per month. Fertilization was more frequent during the spring and summer months. Following fertilization, the plants were rinsed with sufficient clean water to remove residual fertilizer from the leaves. If fertilization frequency, or the concentration of fertilizer, is increased, 'Copito' leaves are darker in color, eventually resulting in burning of leaves and roots. If fertilization frequency, or the concentration of fertilizer, is decreased, 'Copito' leaves are lighter in color. If the ratio of N:K is increased above the value given above, 'Copito' leaves become darker in color, longer and narrower. If the ratio of N:K is decreased below the value given above, 'Copito' leaves become lighter in color, shorter and broader. The intensity of the color of the inflorescence depends also on the amount of P.

With regard to induction of flowering, acetylene gas is allowed to bubble through 100 L of cool water for 30 min. at a pressure of 0.5 bar. Whole plants are then sprayed with the acetylene solution, making certain that the cup (vase) is filled. Spraying is done in the morning because the plants need light after this treatment, and the plants are not watered again for at least two days. The plants are treated again, following this same protocol, one week later. The plants should not be fertilized for two to three weeks following treatment with acetylene because it is likely the flowers will not form and the bracts will remain green. The description of the new cultivar 'Copito' reported herein is based on measurements and observations of plants grown from seeds.

The following traits have been repeatedly observed to be characteristics which, in combination, distinguish Guzmania 'Copito' from the closest comparison cultivar, Guzmania 'Rondo'. The most important difference is the color of the inflorescence. Guzmania 'Copito' is white and Guzmania 'Rondo' is red.

PLANT:
    Form: Funnel-form rosette
    Height: Approximately 20 cm high, when flowering
    Growth Habit: Stemless
    Diameter: Approximately 40 cm
FOLIAGE:
    Color:
        Upper surface: RHS 137A
        Under surface: RHS 137C
        (The color of the leaves can change depending on environmental conditions)
    Size of Leaf:
        Length: Approximately 25 cm
        Width: Approximately 2.0–2.5 cm
    Shape of Leaf: Linear-lanceolate
    Surface Texture: Smooth
    Orientation: Leaf blades arch continuously from the base
BRACTS:
    Length:
        Scape bracts: The lowest are approximately 15 cm long. The scape bracts just below the primary bracts are approximately 6 cm long
        Primary bracts: The lowest are approximately 6 cm long. The bracts progress upwardly, they become shorter, with the top primary bracts being approximately 3 cm in length Width:
  Scape bracts: Approximately 2.0–2.5 cm
  Primary bracts: Approximately 1.5–2.0 cm
Number:
  Scape bracts: Approximately 10
  Primary bracts: Approximately 15
General Shape: Ovate-lanceolate
Texture: Smooth
Margin: Entire
Color: Primary bracts are RHS 160D
FLOWERS:
  Borne (stalks): Erect
  Shape of inflorescence: Singular (head)
  Size of inflorescence on stalk: Approximately 6 cm high and approximately 10 cm in diameter
  Individual petals: (Mostly disposed within the inflorescence)
    Length: Approximately 5 cm
    Width: Approximately 0.5 cm
    Quantity: Approximately 30 flowers depending on the size of the plant
    Color: White
Time of Blooming: A fully grown plant can bloom the whole year starting approximately nine (9) weeks after natural induction or through treatment with acetylene
Duration of blooms: Each flower blooms one (1) day and the total of blooming is approximately five (5) weeks
REPRODUCTIVE ORGANS:
  Ovaries: Superior
  Stamens: Six (6) in number
SEED CHARACTERISTICS:
  Quantity: Approximately 4000 seeds divided over approximately 15 capsules (depending on the size of the plant)
  Texture: Plumose
  Other: This cultivar is a hybrid, and therefore, the seeds cannot be used for reproduction of 'Copito'.

We claim:

1. A seed having American Type Culture Collection Deposit Accession No. PTA-3262 produced by crossing a Guzmania selection identified by Code No. 94861137 with a Guzmania selection identified by Code No. 94861032, said seed producing a plant that is particularly characterized by the following:
   (a) solid growth habit in a funnel-form rosette measuring approximately 20 cm in height above the pot when flowering;
   (b) numerous, relatively narrow leaves, each approximately 2–2.5 cm in width and 25 cm in length;
   (c) superior floral bract production;
   (d) compound inflorescence; and
   (e) long-lasting habit.

2. A Guzmania plant designated cultivar 'Copito' produced from seed accorded American Type Culture Collection Deposit Accession No. PTA-3262.

3. The pollen produced by the plant according to claim 2.

4. The inflorescence produced by the plant according to claim 2.

5. A method of producing Guzmania progeny plant comprising the steps of (a) crossing Guzmania cultivar 'Copito' produced from seed accorded American Type Culture Collection Deposit Accession No. PTA-3262 with another Guzmania plant and (b) selecting progeny.

* * * * *